United States Patent
Kato et al.

(10) Patent No.: US 10,288,414 B2
(45) Date of Patent: May 14, 2019

(54) METHOD FOR MEASURING LAMINATED IRON CORE

(71) Applicant: MITSUI HIGH-TEC, INC., Kitakyushu-shi, Fukuoka (JP)

(72) Inventors: Go Kato, Fukuoka (JP); Takashi Fukumoto, Fukuoka (JP); Kazuki Namaike, Fukuoka (JP); Syoichi Ono, Fukuoka (JP)

(73) Assignee: MITSUI HIGH-TEC, INC., Fukuoka (JP)

( * ) Notice: Subject to any disclaimer, the term of this patent is extended or adjusted under 35 U.S.C. 154(b) by 197 days.

(21) Appl. No.: 15/493,590

(22) Filed: Apr. 21, 2017

(65) Prior Publication Data

US 2017/0307361 A1     Oct. 26, 2017

(30) Foreign Application Priority Data

Apr. 26, 2016  (JP) .................. 2016-087955

(51) Int. Cl.
| | |
|---|---|
| *G01B 11/24* | (2006.01) |
| *H02K 15/03* | (2006.01) |
| *H02K 1/27* | (2006.01) |
| *G01B 11/30* | (2006.01) |
| *G01N 21/954* | (2006.01) |

(52) U.S. Cl.
CPC .......... *G01B 11/24* (2013.01); *H02K 1/2706* (2013.01); *H02K 15/03* (2013.01); *G01B 11/30* (2013.01); *G01N 21/954* (2013.01)

(58) Field of Classification Search
None
See application file for complete search history.

(56) References Cited

U.S. PATENT DOCUMENTS

| | | | |
|---|---|---|---|
| 2010/0284027 A1* | 11/2010 | Scheiner ................ | G01B 11/22 356/626 |
| 2011/0000079 A1* | 1/2011 | Fukumaru ............ | H02K 1/2766 29/598 |

(Continued)

FOREIGN PATENT DOCUMENTS

| | | |
|---|---|---|
| JP | 11-55906 | 2/1999 |
| JP | 2008092770 A * | 4/2008 |
| JP | 2010-263757 | 11/2010 |

OTHER PUBLICATIONS

Akiyama et al., "Development of Optical Measuring Equipment for Diameter of Small and Deep Holes" J-STAGE, vol. 62, No. 4, 1996 (Year: 1996).*

(Continued)

*Primary Examiner* — John C Kuan
(74) *Attorney, Agent, or Firm* — Greenblum & Bernstein, P.L.C.

(57) ABSTRACT

There is provided a method for measuring a laminated iron core. The method includes preparing a laminated iron core in which two or more kinds of metal plates with different shapes are laminated and a deformed part is formed inside a hole continuing in a lamination direction of the laminated iron core, acquiring a surface profile data indicating a surface shape of the deformed part through an inlet of the hole by a non-contact sensor located in an outside of the hole, and calculating a size of the deformed part by a calculator based on the surface profile data.

20 Claims, 11 Drawing Sheets

(56) References Cited

U.S. PATENT DOCUMENTS

2012/0042934 A1* 2/2012 Nasuno ................ H01L 22/12
                                                                     136/249
2012/0069351 A1* 3/2012 Glasenapp ............ G01B 11/12
                                                                     356/602

OTHER PUBLICATIONS

Wakayama et al., "Development of a compact inner profile measuring instrument" Proc. of SPIE vol. 6762, 2007 (Year: 2007).*

* cited by examiner

METHOD FOR MEASURING LAMINATED IRON CORE

CROSS REFERENCE TO RELATED APPLICATION

This application is based upon and claims the benefit of priority of Japanese Patent Application No. 2016-087955 filed on Apr. 26, 2016, the contents of which are incorporated herein by reference in its entirety.

BACKGROUND OF THE INVENTION

1. Field of the Invention

The present disclosure relates to a method for measuring a laminated iron core.

2. Description of the Related Art

A laminated iron core is a component constructing a motor (electric motor), and forms a rotor or a stator of the motor. The laminated iron core is obtained by stacking a plurality of metal plates (blanked members) blanked from an electromagnetic steel plate in a predetermined shape and interlocking the metal plates. A coil is wound on a stator laminated iron core forming the stator. A shaft and a permanent magnet are installed in a rotor laminated iron core forming the rotor. Thereafter, the stator and the rotor are combined to complete the motor. The motor adopting the laminated iron core is used as, for example, driving sources of a refrigerator, an air conditioner, a hard disk drive, an electric power tool, a hybrid car, an electric vehicle, etc.

The laminated iron core is generally manufactured by a forward die unit. A step of intermittently blanking a strip-shaped electromagnetic steel plate and obtaining a blanked member and a step of stacking the plurality ofity of blanked members to a predetermined lamination thickness and obtaining a laminated iron core are performed inside the forward die unit. The laminated iron core ejected from the forward die unit requires that the thickness (lamination thickness) of the laminated iron core should be within a predetermined tolerance. However, a plate thickness of the strip-shaped electromagnetic steel plate is not always uniform. That is, the strip-shaped electromagnetic steel plate has a deviation of the plate thickness. As a result, there are cases where the thickness of the laminated iron core is not within the tolerance under the influence of the deviation of the plate thickness in the case of simply laminating a predetermined number of blanked members.

JP-A-11-55906 as Patent Literature 1 discloses a method for manufacturing a laminated iron core having a counter bore in which a shaft hole is provided with a step. The laminated iron core described in JP-A-11-55906 is constructed by combining two or more kinds of blanked members with different shapes. The manufacturing method described in JP-A-11-55906 uses a control program for correcting the number of laminations by specifying one of the counter bores excluding the counter bore in which the number of laminations is specified. JP-A-2010-263757 as Patent Literature 2 discloses a laminated iron core in which a refrigerant flow path is formed inside a shaft hole as another example of the laminated iron core constructed by combining two or more kinds of blanked members with different shapes. Note that, in the present specification, the laminated iron core in which two or more kinds of blanked members with different shapes are laminated and a deformed part such as a projection, a recess or a hole is formed inside a hole continuing in a lamination direction (axial direction) may be called a "laminated iron core with deformed part".

Patent Literature 1: JP-A-11-55906
Patent Literature 1: JP-A-2010-263757

SUMMARY OF THE INVENTION

In the laminated iron core described in JP-A-11-55906 or JP-A-2010-263757, etc., it is decided whether or not the deformed part has a desired size by using the number of laminations of the blanked members. However, in recent years, a demand for high quality of the laminated iron core has increased more, and it is desirable to acquire the size of the deformed part with high accuracy.

Hence, the present disclosure describes a method for measuring a laminated iron core capable of acquiring a size of a deformed part with high accuracy.

(1) A method for measuring a laminated iron core according to an aspect of the present disclosure includes: preparing a laminated iron core in which two or more kinds of metal plates with different shapes are laminated and a deformed part is formed inside a hole continuing in a lamination direction of the laminated iron core; acquiring a surface profile data indicating a surface shape of the deformed part through an inlet of the hole by a non-contact sensor located in an outside of the hole; and calculating a size of the deformed part by a calculator based on the surface profile data.

The hole continuing in the lamination direction of the laminated iron core is generally small to the extent to which it is difficult for a contact sensor to enter the inside of the hole, and the deformed part of the inside of the hole cannot be measured by the contact sensor. However, in the method for measuring the laminated iron core according to one aspect of the present disclosure, the non-contact sensor located in the outside of the hole acquires the surface profile data indicating the surface shape of the deformed part through the inlet of the hole. As a result, the non-contact sensor directly acquires the surface profile data of the deformed part from the outside of the hole without facing the deformed part. Also, in the method for measuring the laminated iron core according to one aspect of the present disclosure, the calculator calculates the size of the deformed part based on the surface profile data. Thus, in the method for measuring the laminated iron core according to one aspect of the present disclosure, the size of the deformed part is directly acquired using the non-contact sensor rather than the number of laminations of the metal plates. Consequently the size of the deformed part can be acquired with high accuracy.

(2) In the method for measuring the laminated iron core according to the method (1), the surface profile data indicating the surface shape of the deformed part may be acquired by the non-contact sensor located in the outside of the hole through the inlet of the hole, with the laminated iron core pressurized in the lamination direction.

A finished product of the laminated iron core may be obtained by completely bonding the mutual blanked members by welding etc. with the laminated iron core pressurized in the lamination direction after the laminated iron core is measured. In this case, a size equal to that of the deformed part in the finished product can be acquired by acquiring the surface profile data with the laminated iron core pressurized in the lamination direction as described above.

(3) The method for measuring the laminated iron core according to the method (1) or (2) may be configured such that the non-contact sensor is a non-contact laser displacement meter, and the surface profile data indicating the surface shape of the deformed part is acquired by the non-contact laser displacement meter located in the outside of the hole, which applies laser light from the inlet of the hole to the deformed part and receives reflected light of the laser light.

(4) The method for measuring the laminated iron core according to any one of the methods (1) to (3) may be configured such that the deformed part is a projected part projected from a peripheral surface of the hole in an intersection direction intersecting with the lamination direction.

(5) The method for measuring the laminated iron core according to any one of the methods (1) to (3) may be configured such that the deformed part is a branched hole continuing from a peripheral surface of the hole in an intersection direction intersecting with the lamination direction so as to be branched from the hole.

(6) The method for measuring the laminated iron core according to any one of the methods (1) to (5) may further include moving or rotating one of the laminated iron core or the non-contact sensor with respect to the other of the laminated iron core and the non-contact sensor.

In this case, one of the laminated iron core and the non-contact sensor is moved or rotated with respect to the other of the laminated iron core and the non-contact sensor, with the result that the non-contact sensor acquires the surface profiles of the plurality of deformed parts at once when the laminated iron core is provided with the plurality of deformed parts. As a result, the sizes of the plurality of deformed parts can be acquired at once with high accuracy.

(7) The method for measuring the laminated iron core according to any one of the methods (1) to (6) may be configured such that a length of the deformed part in the lamination direction is calculated by the calculator based on the surface profile data.

(8) The method for measuring the laminated iron core according to any one of the methods (1) to (6) may be configured such that a length of the deformed part in a circumferential direction of the hole is calculated by the calculator based on the surface profile data.

(9) The method for measuring the laminated iron core according to any one of the methods (1) to (8) may be configured such that a length from the inlet of the hole to the deformed part in the lamination direction is calculated by the calculator based on the surface profile data.

(10) The method for measuring the laminated iron core according to any one of the methods (1) to (9) may be configured such that the deformed part is a projected part projected from a peripheral surface of the hole in an intersection direction intersecting with the lamination direction, and a projection length of the projected part is calculated by the calculator based on the surface profile data.

(11) A system for measuring a laminated iron core according to an aspect of the present disclosure includes: a controller; a pinching plate pinching a laminated iron core in which two or more kinds of metal plates with different shapes are laminated and a deformed part is formed inside a hole continuing in a lamination direction of the laminated iron core, the pinching plate including a through hole; a non-contact sensor located in an outside of the through hole of the pinching plate, the controller acquiring a surface profile data indicating a surface shape of the deformed part through an inlet of the hole of the laminated iron core and the through hole of the pinching plate by the non-contact sensor, and calculating a size of the deformed part based on the surface profile data.

The method or system for measuring the laminated iron core according to the present disclosure can acquire the size of the deformed part with high accuracy.

DETAILED DESCRIPTION OF THE EXEMPLARY EMBODIMENTS

Figure 1:
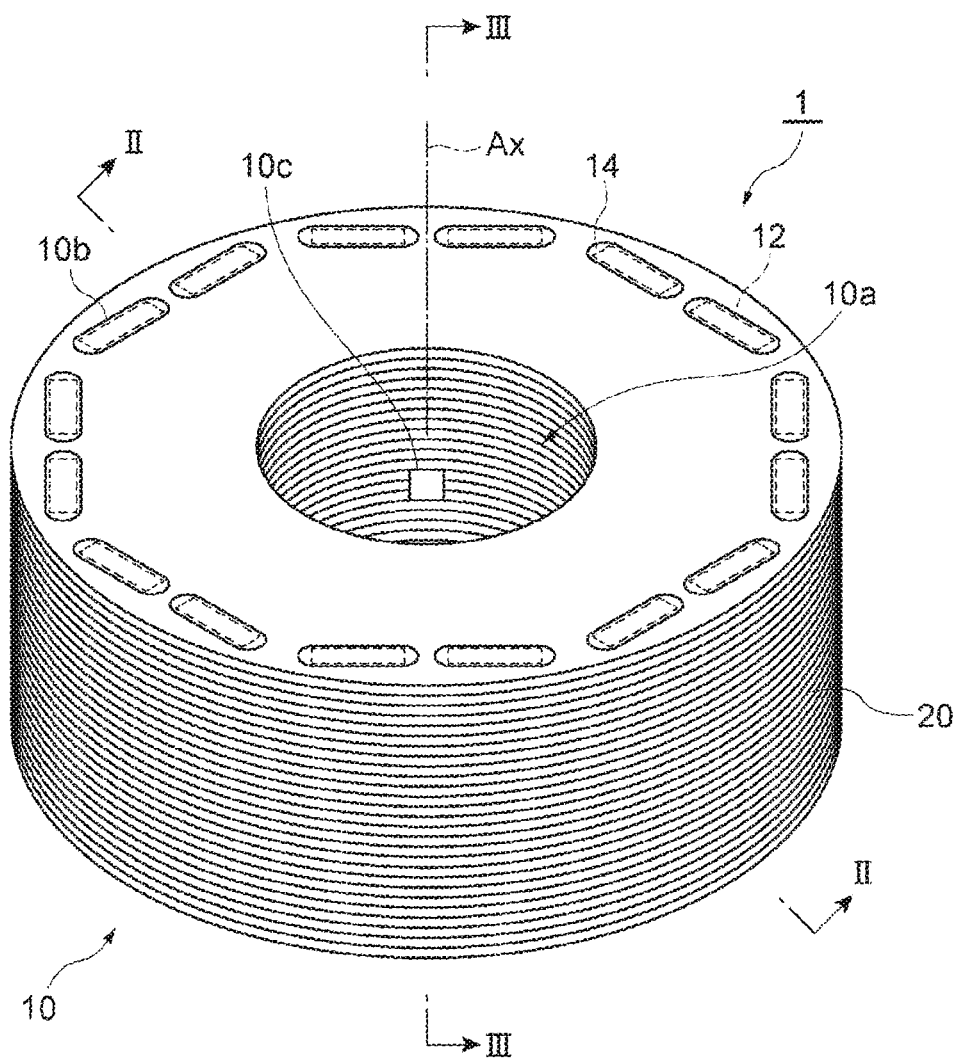
FIG. 1 is a perspective view showing one example of a rotor.

An embodiment according to the present disclosure described below is an illustration for describing the present invention. Thus, the present invention should not be limited to the following embodiments or contents. In the following description, the same reference sign or numeral is used for the same element or an element having the same function, and overlap description is omitted.

(Configuration of Rotor)

First, a configuration of a rotor 1 will be described with reference to FIGS. 1 to 3. The rotor 1 constructs a motor (electric motor) together with a stator. The rotor 1 includes a laminated iron core 10, a plurality of permanent magnets 12, a plurality of resin materials 14, and a shaft (not shown).

The laminated iron core 10 is a laminated body formed by laminating a plurality of blanked members 20 (metal plates) formed by blanking a strip-shaped electromagnetic steel plate (not shown). The laminated iron core 10 has two or more kinds of blanked members 20 with different shapes. The blanked members 20 are mutually bonded by caulking, welding, etc.

The laminated iron core 10 has a circular cylindrical shape. That is, the center of the laminated iron core 10 is provided with a shaft hole 10*a* pierced in the laminated iron core 10 so as to be continuous along a central axis Ax. That is, the shaft hole 10*a* continues in a lamination direction (hereinafter simply called a "lamination direction") of the laminated iron core 10. The lamination direction is also an extension direction of the central axis Ax. A shaft is inserted into the shaft hole 10*a*.

The laminated iron core 10 is formed with a plurality of magnet-insert holes 10*b* and a plurality of deformed parts 10*c*. The magnet-insert holes 10*b* are arranged at predetermined distances along an outer peripheral edge of the laminated iron core 10 as shown in FIG. 1. The magnet-insert holes 10*b* are pierced in the laminated iron core 10 so as to continue or be continuous along the central axis Ax as shown in FIG. 2. That is, the magnet-insert holes 10*b* continues in the lamination direction.

The shape of the magnet-insert hole 10*b* is an elongate hole continuing along the outer peripheral edge of the laminated iron core 10 in the embodiment. The number of magnet-insert holes 10*b* is sixteen in the embodiment. Positions, shapes and the number of magnet-insert holes 10*b* may be changed depending on, for example, required performance or use of the motor.

The inside of the magnet-insert hole 10*b* is provided with a plurality of projections 10*d*. The projection 10*d* is projected along a radial direction (hereinafter simply called a "radial direction") of the laminated iron core 10 outwardly from a surface (an inside inner peripheral surface) near to the central axis Ax in an inner peripheral surface of the magnet-insert hole 10*b*. That is, the projection 10*d* extends in an intersection direction (radial direction) intersecting with the lamination direction outwardly from the inside inner peripheral surface. The projections 10*d* are arranged at predetermined distances in the extension direction (lamination direction) of the magnet-insert hole 10*b*.

The deformed part 10*c* is arranged inside the shaft hole 10*a*. The deformed part 10*c* is a recessed part recessed from an inner peripheral surface of the shaft hole 10*a* toward the radial outside as shown in FIG. 3. That is, the deformed part 10*c* extends in the radial direction outwardly from the shaft hole 10*a*. The deformed part 10*c* of the embodiment is one form of a branched hole radially continuing from the inner peripheral surface of the shaft hole 10*a* so as to be branched from the shaft hole 10*a*.

The shape of the deformed part 10*c* is a rectangular shape when viewed from the radial direction in the embodiment. The number of deformed parts 10*c* is two in the embodiment, and a pair of the deformed parts 10*c* is positioned symmetrically with respect to the central axis Ax. The shapes and the number of deformed parts 10*c* may be changed according to, for example, required performance or use of the motor.

Figure 2:
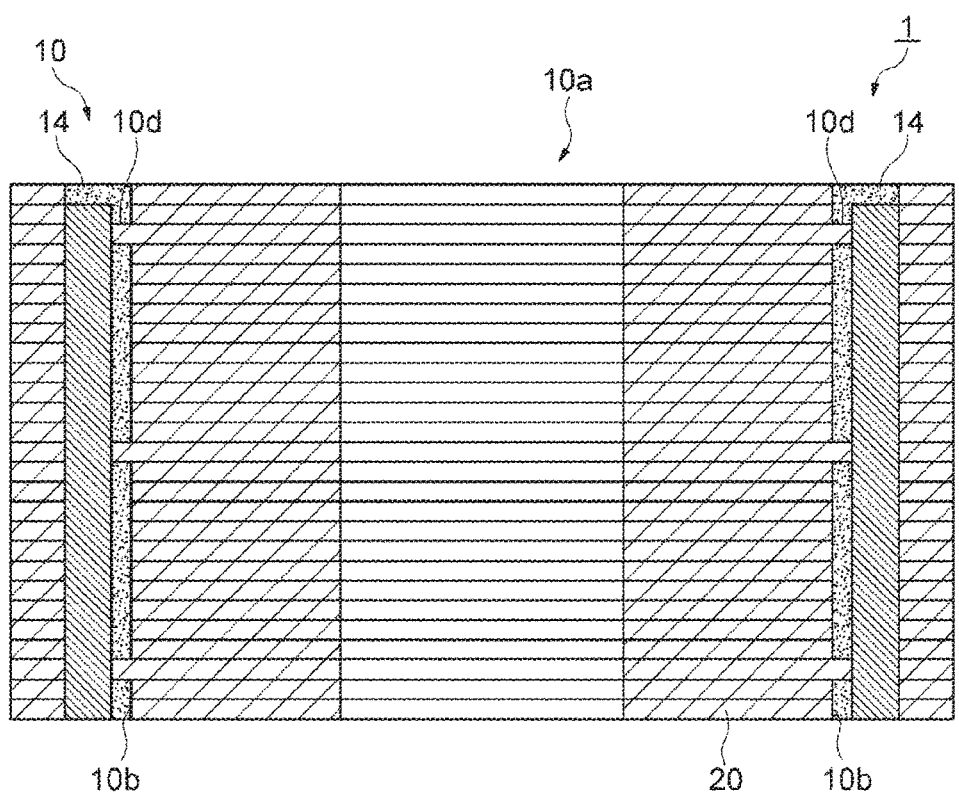
FIG. 2 is a sectional view taken on line II-II of FIG. 1.
Figure 3:
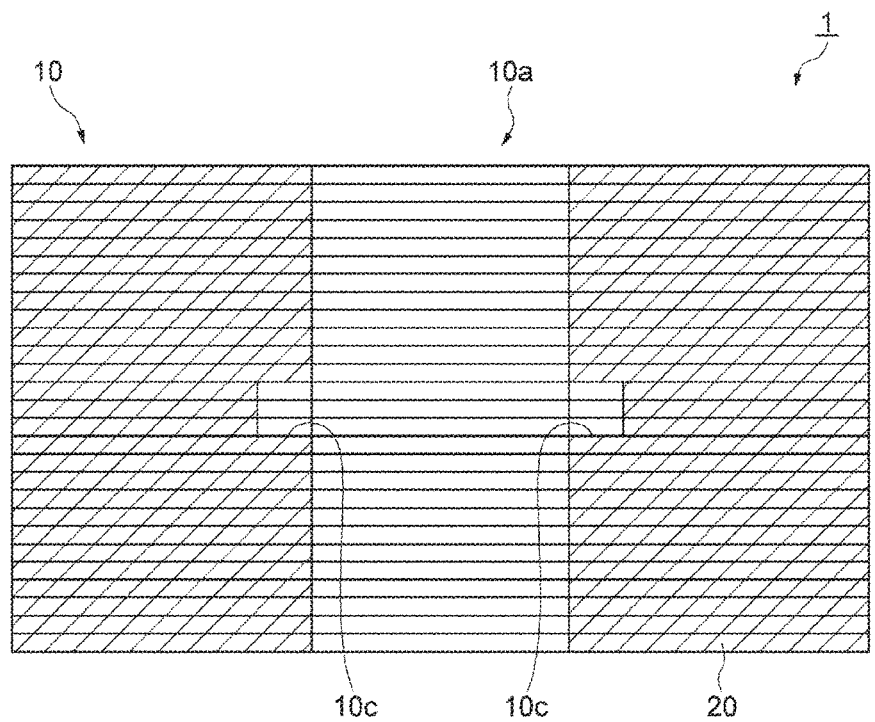
FIG. 3 is a sectional view taken on line III-III of FIG. 1.

The permanent magnet 12 is inserted into the magnet-insert hole 10*b* as shown in FIGS. 1 and 2. The permanent magnet 12 is pinched by the projection 10*d* and a surface (an outside inner peripheral surface) near to the outer peripheral edge of the laminated iron core 10 in the inner peripheral surface of the magnet-insert hole 10*b* inside the magnet-insert hole 10*b* as shown in FIG. 2. The number of permanent magnets 12 inserted into the magnet-insert hole 10*b* may be one or more. The plurality of permanent magnets 12 may be arranged in a circumferential direction of the laminated iron core 10 or in the lamination direction inside the magnet-insert hole 10*b*. A kind of permanent magnet 12 could be determined according to, for example, required performance or use of the motor, and may be a sintered magnet or a bonded magnet.

The inside of the magnet-insert hole 10*b* after the permanent magnet 12 is inserted is filled with the resin material 14. The resin material 14 has a function of fixing the permanent magnet 12 into the magnet-insert hole 10*b*. The resin material 14 includes, for example, a thermosetting resin. A concrete example of the thermosetting resin includes, for example, a resin composition including an additive, a curing initiator, and an epoxy resin. The additive includes, for example, a filler, a flame retardant or a stress relaxation agent. The resin material 14 mutually bonds the blanked members 20 adjacent in a vertical direction. In addition, a thermoplastic resin may be used as the resin material 14.

(Method for Measuring Laminated Iron Core)

Figure 4:
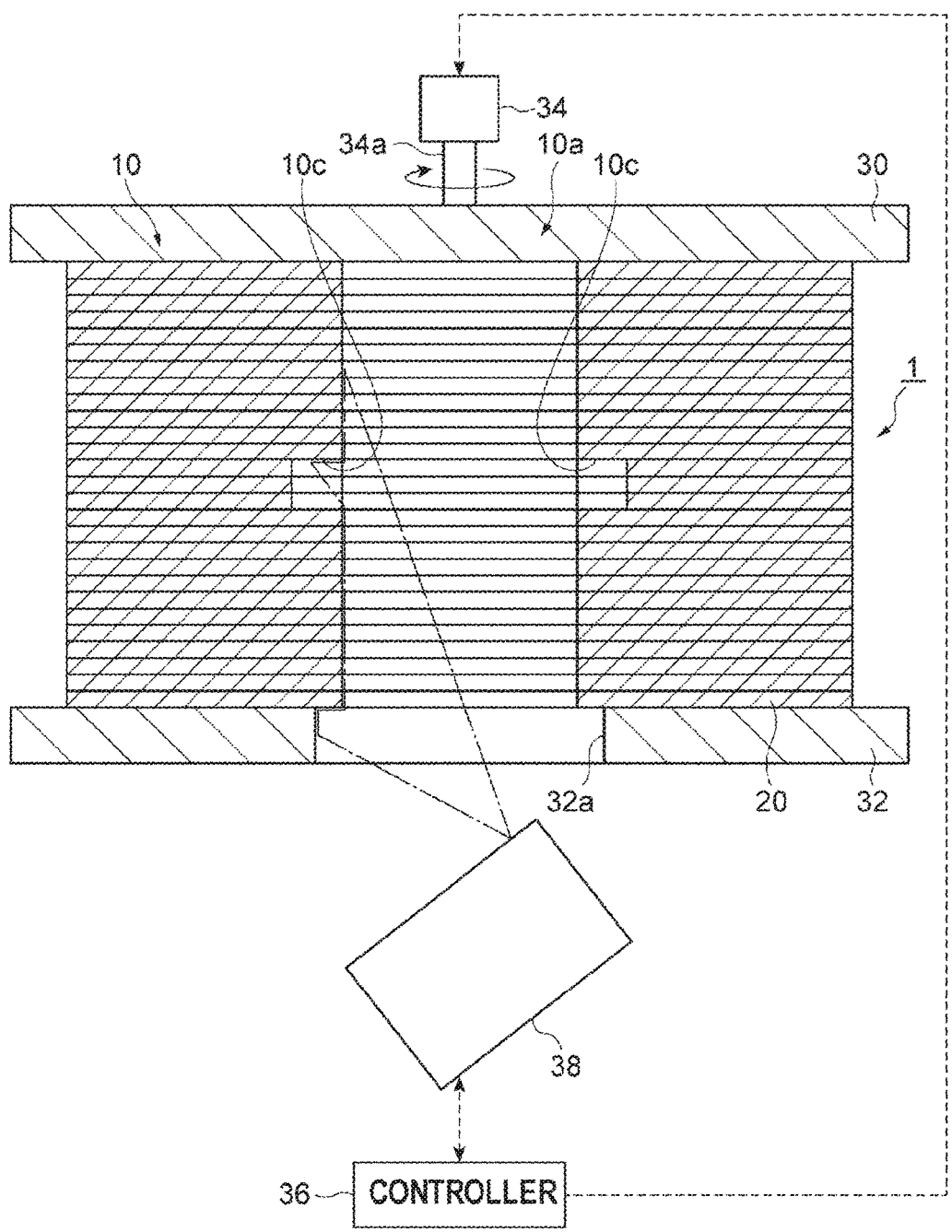
FIG. 4 is an explanatory diagram of one example of a method for measuring a deformed part.

Subsequently, a method for measuring the laminated iron core 10 will be described with reference to FIGS. 4 and 5. First, as shown in FIG. 4, the laminated iron core 10 is pinched in the lamination direction by a pair of pinching plates 30, 32. Accordingly, the laminated iron core 10 is pressurized in its lamination direction by the pinching plates 30, 32 to the extent to which the adjacent blanked members 20 make close contact with each other. The pressure applied to the laminated iron core 10 by the pinching plates 30, 32 can have various intensities depending on the size of the laminated iron core 10, and may have, for example, the intensity in which a thickness T of the laminated iron core 10 after pressurization satisfies values from 99.9% of a thickness $T_0$ (inclusive) of the laminated iron core 10 before pressurization to the thickness $T_0$ (exclusive) ($0.999T_0 \leq T < T_0$). In the embodiment, the pinching plate 30 abuts on one end face (upper surface of FIG. 4) of the laminated iron core 10, and the pinching plate 32 abuts on the other end face (lower surface of FIG. 4) of the laminated iron core 10.

An actuator 34 is connected to the pinching plate 30 through a shaft 34*a* extending along the central axis Ax. The actuator 34 drives and stops rotation according to a driving signal from a controller 36 (calculator). The center of the pinching plate 32 is provided with a through hole 32*a* larger than the shaft hole 10*a*. With the laminated iron core 10 pinched by the pinching plates 30, 32, the through hole 32*a* communicates with the shaft hole 10*a*.

Next, a non-contact sensor 38 is prepared. Concretely, the non-contact sensor 38 is arranged under the through hole 32*a* of the pinching plate 32 so that a sending and receiving part for a detection signal faces to the side of one deformed part 10*c* targeted for detection through an inlet of the shaft hole 10*a*. That is, the non-contact sensor 38 is located in the outside of the shaft hole 10*a*. As the non-contact sensor 38, various sensors can be used as long as a surface profile data indicating a surface shape of an object to be measured can be acquired without contact with the object to be measured, and the non-contact sensor 38 includes, for example, a non-contact laser displacement meter or an ultrasonic displacement meter. The non-contact laser displacement meter includes a light source for emitting laser light, and a light receiving element for receiving reflected light, and calculates a distance to the object to be measured based on, for example, an imaging position or the amount of light in the light receiving element. The ultrasonic displacement meter includes a wave sender for sending ultrasonic waves, and a wave receiver for receiving the reflected waves, and calculates a distance to the object to be measured based on the time taken to receive the ultrasonic wave since the ultrasonic wave is sent.

Then, the controller 36 sends a driving signal to the non-contact sensor 38, and sends, for example, a detection signal diffused in the lamination direction from the non-contact sensor 38, and the non-contact sensor 38 receives a reflected signal of the detection signal and thereby the non-contact sensor 38 is made to acquire a surface profile of the deformed part 10*c*. In the embodiment, the laminated iron core 10 is rotated, with the result that the non-contact sensor 38 acquires a surface profile data of an inner peripheral surface of the shaft hole 10*a* in addition to the surface profile data of the deformed part 10*c*. The surface profile data (or simply called "surface profile") acquired by the non-contact sensor 38 is sent to the controller 36. FIG. 5 shows one example of a surface profile P of the deformed part 10*c* acquired by the non-contact sensor 38.

Figure 5:
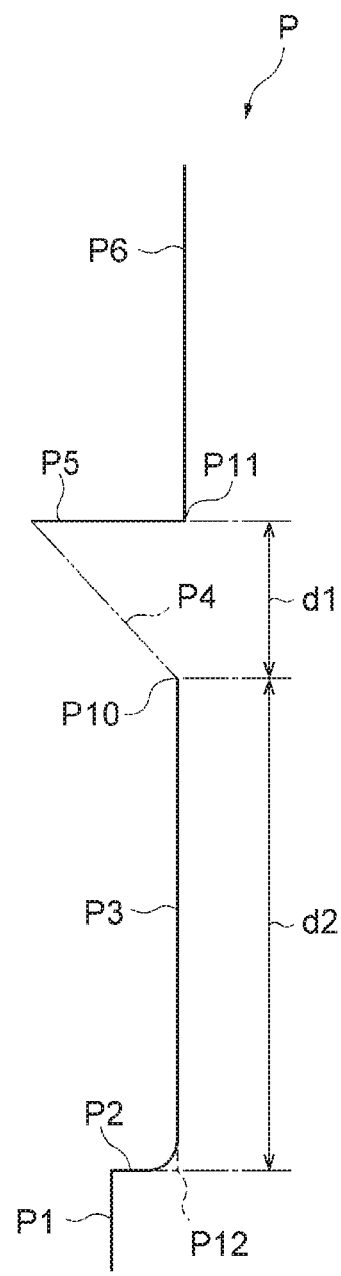
FIG. 5 is an explanatory diagram of one example of the method for measuring the deformed part.

The surface profile P shown in FIG. 5 as one example includes line segments P1 to P6. The line segment P1 corresponds to an inner peripheral surface of the through hole 32a, and extends in a vertical direction of FIG. 5. The line segment P2 corresponds to a region exposed from the through hole 32a in a lower surface of the laminated iron core 10, and extends in a horizontal direction of FIG. 5. The line segment P3 corresponds to a region from the lower surface (inlet of the shaft hole 10a) of the laminated iron core 10 to the deformed part 10c in the inner peripheral surface of the shaft hole 10a, and extends in the vertical direction of FIG. 5.

The line segment P4 is a virtual line showing the boundary between a region in which a detection signal of the non-contact sensor 38 reaches the inside of the deformed part 10c and a region in which the detection signal of the non-contact sensor 38 becomes a blind spot inside the deformed part 10c, and extends from an upper end point of the line segment P3 to the left oblique upward side in FIG. 5. The line segment P5 corresponds to an inner wall surface (upper wall surface) of the deformed part 10c, and extends in the horizontal direction of FIG. 5. The line segment P6 corresponds to a region of the side upper than the deformed part 10c in the inner peripheral surface of the shaft hole 10a, and extends in the vertical direction of FIG. 5.

Then, the controller 36 calculates a size of the deformed part 10c based on data of the surface profile P sent from the non-contact sensor 38. The calculated size of the deformed part 10c includes, for example, a height (length of the deformed part 10c in the lamination direction) d1 of the deformed part 10c, and a length d2 from the lower surface (inlet of the shaft hole 10a) of the laminated iron core 10 to the deformed part 10c in the lamination direction.

The controller 36 calculates the height d1, for example, by obtaining a linear distance between an upper end point P10 of the line segment P3 and a lower end point P11 of the line segment P6 based on the surface profile P. The upper end point P10 is also a point of intersection between the line segment P3 and the virtual line segment P4. The lower end point P11 is also a point of intersection between the line segments P5, P6. The controller 36 calculates the length d2, for example, by obtaining a length of the line segment P3 based on the surface profile P.

In addition, when the peripheral edge of the blanked member 20 is round due to, for example, blanking by a punch (when a shear drop surface occurs), the corner formed of the line segments P2, P3 is similarly round, with the result that the length d2 may be calculated from a point P12 of intersection between mutual extended virtual lines with the line segments P2, P3 extended rather than the length of the line segment P3 itself. Similarly, when the peripheral edge of the blanked member 20 has projections due to, for example, blanking by a punch (when burrs occur), the length d2 may be calculated from the point P12 of intersection between the mutual extended virtual lines with the line segments P2, P3 extended.

Then, with the laminated iron core 10 pinched by the pinching plates 30, 32, the controller 36 sends a driving signal to the actuator 34, and rotates the pinching plate 30 by the actuator 34 through the shaft 34a. At this time, the laminated iron core 10 is pinched by the pinching plates 30, 32, with the result that the laminated iron core 10 and the pinching plate 32 are also rotated with rotation of the pinching plate 30 by the actuator 34. When the sending and receiving part for the detection signal faces to the side of another deformed part 10c targeted for detection through the inlet of the shaft hole 10a, the controller 36 sends a stop signal to the actuator 34, and stops operation of the actuator 34. Thereafter, the controller 36 acquires a size of another deformed part 10c in a manner similar to the above.

(Action)

Incidentally, the shaft hole 10a continuing in the lamination direction is generally small to the extent to which it is difficult for a contact sensor to enter the inside of the shaft hole 10a, and the deformed part 10c of the inside of the shaft hole 10a cannot be measured by the contact sensor. However, in the embodiment, the non-contact sensor 38 located in the outside of the shaft hole 10a acquires the surface profile P corresponding to a surface shape of the deformed part 10c through the inlet of the shaft hole 10a. As a result, the non-contact sensor 38 directly acquires the surface profile P of the deformed part 10c from the outside of the shaft hole 10a without facing the deformed part 10c. Also, in the embodiment, the controller 36 calculates the size of the deformed part 10c based on the surface profile P. Thus, in the embodiment, the size of the deformed part 10c is directly acquired using the non-contact sensor 38 rather than the number of laminations of the blanked members 20. Consequently, the size of the deformed part 10c can be acquired with high accuracy.

Incidentally, a finished product of the laminated iron core 10 may be obtained by completely bonding the mutual blanked members 20 by welding etc. with the laminated iron core 10 pressurized in the lamination direction of the laminated iron core 10 after the laminated iron core 10 is measured. Here, in the embodiment, in the case of measuring the laminated iron core 10, the non-contact sensor located in the outside of the shaft hole 10a acquires the surface profile P corresponding to the surface shape of the deformed part 10c through the inlet of the shaft hole 10a with the laminated iron core 10 pressurized in the lamination direction of the laminated iron core 10. As a result, a size equal to that of the deformed part 10c in the finished product can be acquired.

In the embodiment, the sizes of the plurality of deformed parts 10c are respectively acquired by rotating the laminated iron core 10 with respect to the non-contact sensor 38. As a result, since the laminated iron core 10 is rotated with respect to the non-contact sensor 38, the non-contact sensor 38 acquires the surface profiles P of these a plurality of deformed parts 10c at once when the laminated iron core 10 is provided with the plurality of deformed parts 10c. Consequently, the sizes of the plurality of deformed parts 10c can be acquired at once with high accuracy.

(Other Embodiments)

Figure 6:
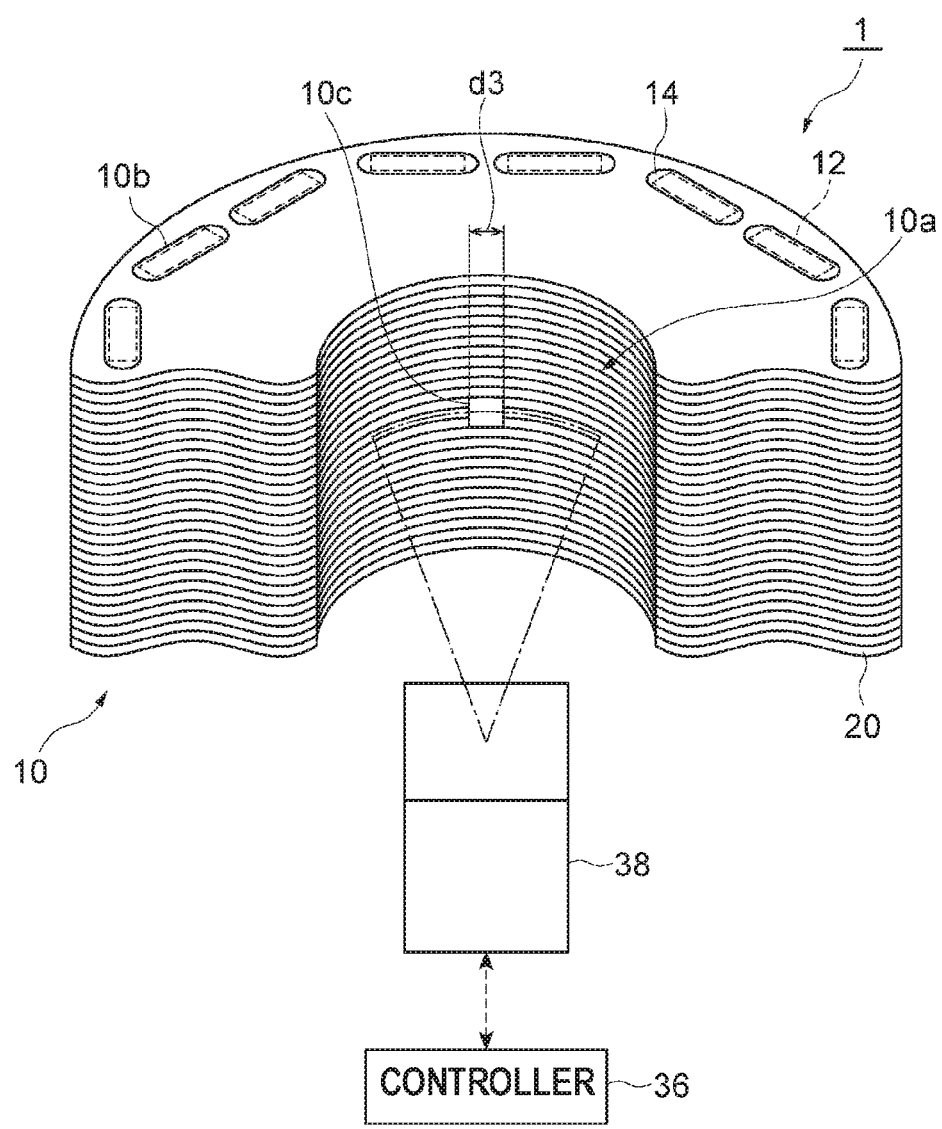
FIG. 6 is an explanatory diagram of another example of a method for measuring a deformed part.

The embodiment according to the present disclosure has been described above in detail, but various modifications may be made in the embodiment described above within the scope of the gist of the present invention. For example, the controller 36 may calculate a width (length of the deformed part 10c in a circumferential direction of the shaft hole 10a) d3 of the deformed part 10c as shown in FIG. 6 as information about the deformed part 10c. In this case, the controller 36 sends a driving signal to the non-contact sensor 38, and sends, for example, a detection signal diffused in a radial direction from the non-contact sensor 38, and the non-contact sensor 38 receives a reflected signal of the detection signal and thereby, the non-contact sensor 38 is made to acquire a surface profile of the deformed part 10c.

Figure 7:
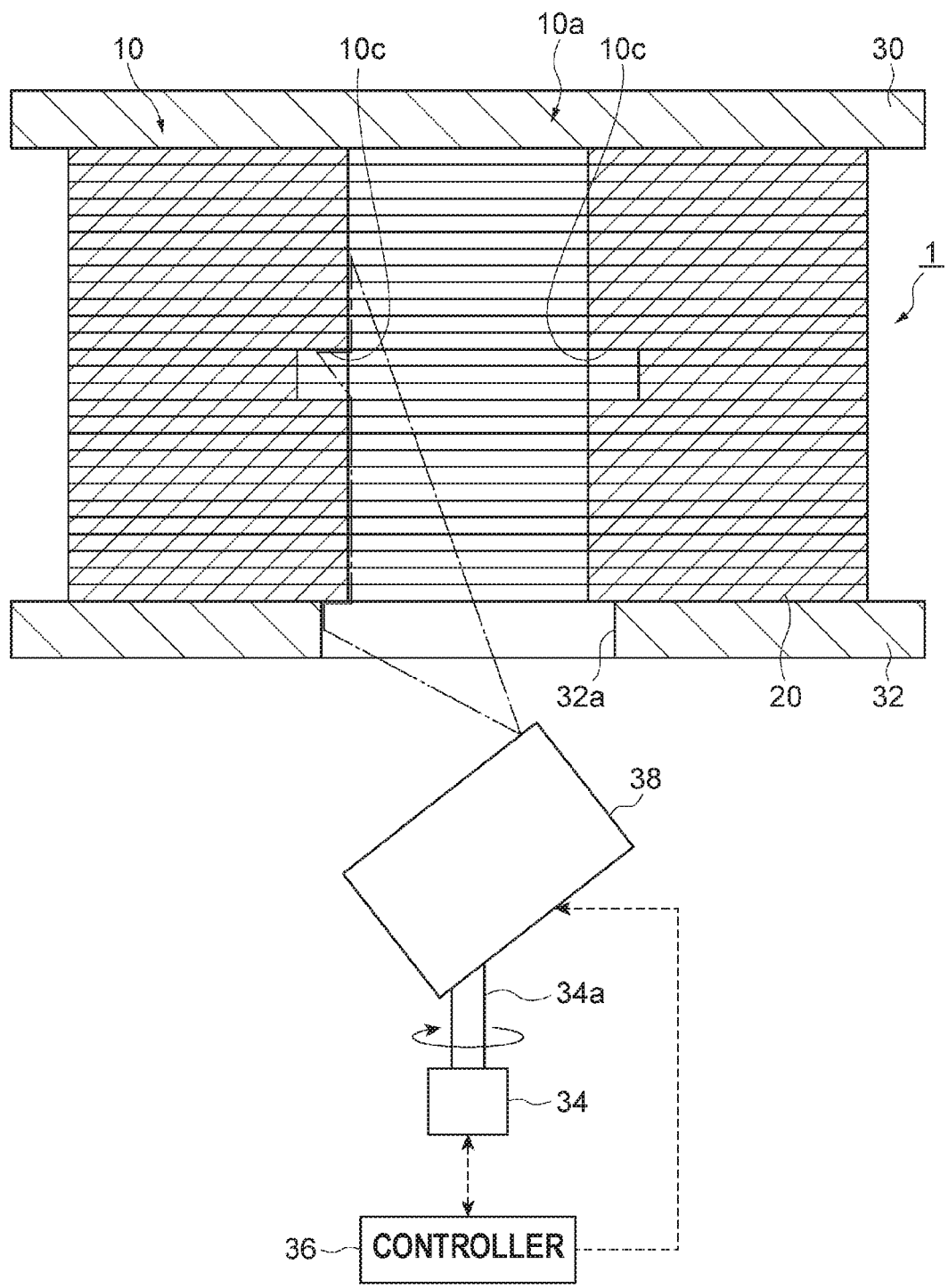
FIG. 7 is an explanatory diagram of a further example of a method for measuring a deformed part.

As shown in FIG. 7, the shaft 34a may be connected to the non-contact sensor 38, and the actuator 34 may rotate the non-contact sensor 38 through the shaft 34a. That is, in the case of acquiring the surface profile P of the deformed part 10c by the non-contact sensor 38, with the laminated iron core 10 pinched by the pinching plates 30, 32, the controller 36 may send a driving signal to the actuator 34, and the actuator 34 may rotate the non-contact sensor 38 through the shaft 34a.

In other words, in the case of acquiring the surface profile P of the deformed part 10c by the non-contact sensor 38, one of the laminated iron core 10 and the non-contact sensor 38 may be rotated with respect to the other of the laminated iron core 10 and the non-contact sensor 38. In the case of acquiring the surface profile P of the deformed part 10c by the non-contact sensor 38, one of the laminated iron core 10 and the non-contact sensor 38 may be moved with respect to the other of the laminated iron core 10 and the non-contact sensor 38 (displacement other than rotation may be performed).

Alternatively, the non-contact sensor 38 located in the outside of the shaft hole 10a may acquire the surface profile P of the deformed part 10c through the inlet of the shaft hole 10a while rotating one of the laminated iron core 10 and the non-contact sensor 38 with respect to the other of the laminated iron core 10 and the non-contact sensor 38. The non-contact sensor 38 located in the outside of the shaft hole 10a may acquire the surface profile P of the deformed part 10c through the inlet of the shaft hole 10a while moving one of the laminated iron core 10 and the non-contact sensor 38 with respect to the other of the laminated iron core 10 and the non-contact sensor 38 (while performing displacement other than rotation). The number of rotations at this time may be set at a proper value according to performance (for example, a sampling rate) of the non-contact sensor 38.

Figure 8:
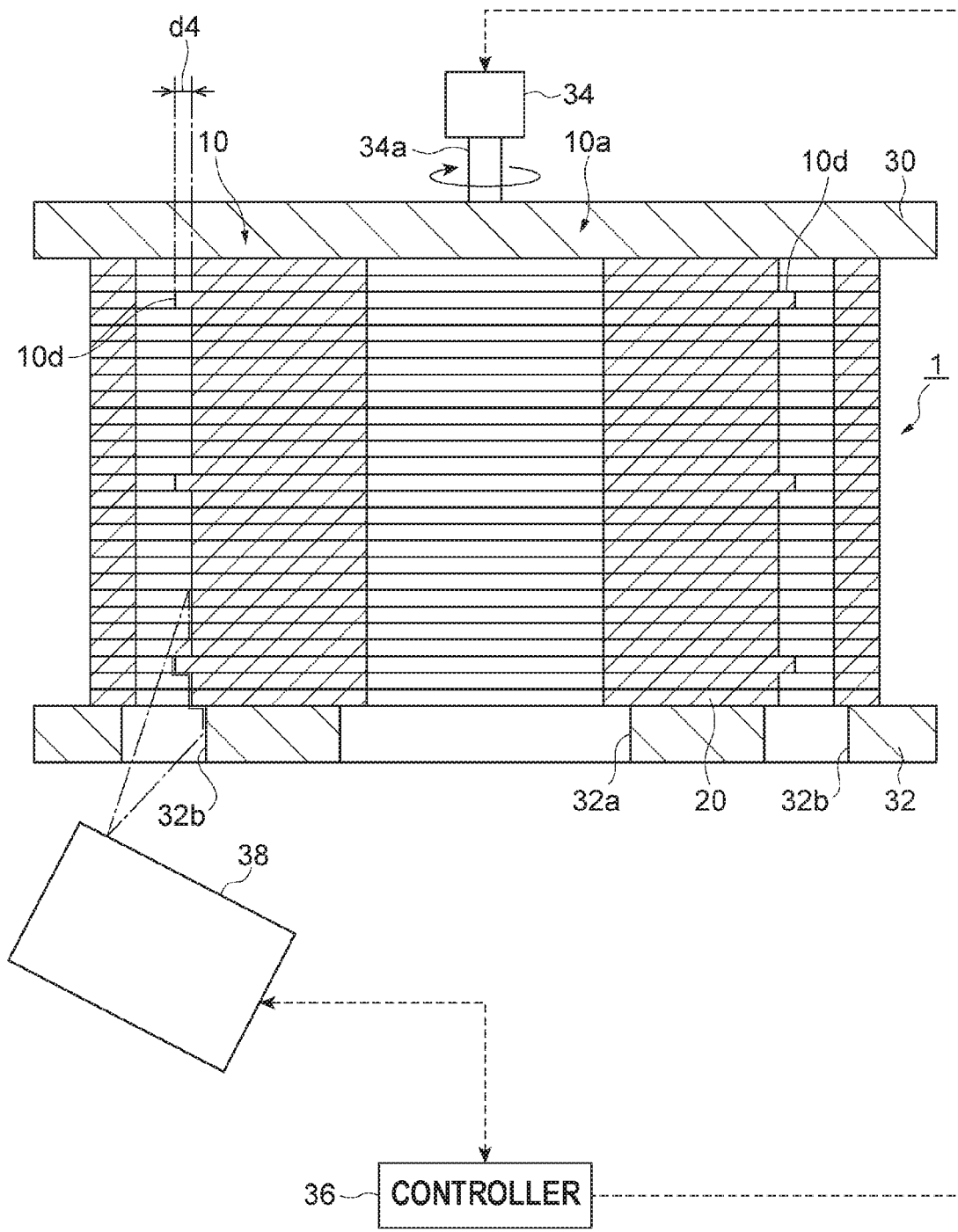
FIG. 8 is an explanatory diagram of a further example of a method for measuring a deformed part.

As shown in FIG. 8, the non-contact sensor 38 may acquire a surface profile of the projection 10d of the inside of the magnet-insert hole 10b and the controller 36 may calculate a size of the projection 10d. That is, the projection 10d can also be said to be a deformed part present inside the magnet-insert hole 10b. The size of the projection 10d calculated by the controller 36 includes, for example, a projection length d4 of the projection 10d in addition to a height of the projection 10d, a length from a lower surface (inlet of the magnet-insert hole 10b) of the laminated iron core 10 to the projection 10d in the lamination direction, and a width of the projection 10d like the deformed part 10c.

In the case of acquiring the surface profile of the projection 10d by the non-contact sensor 38, the pinching plate 32 is provided with a through hole 32b larger than the magnet-insert hole 10b in a place corresponding to the magnet-insert hole 10b. With the laminated iron core 10 pinched by the pinching plates 30, 32, the through hole 32b communicates with the magnet-insert hole 10b. The non-contact sensor 38 is arranged under the through hole 32b of the pinching plate 32 so that a sending and receiving part for a detection signal faces to the side of the projection 10d targeted for detection through the inlet of the magnet-insert hole 10b.

Figure 9:
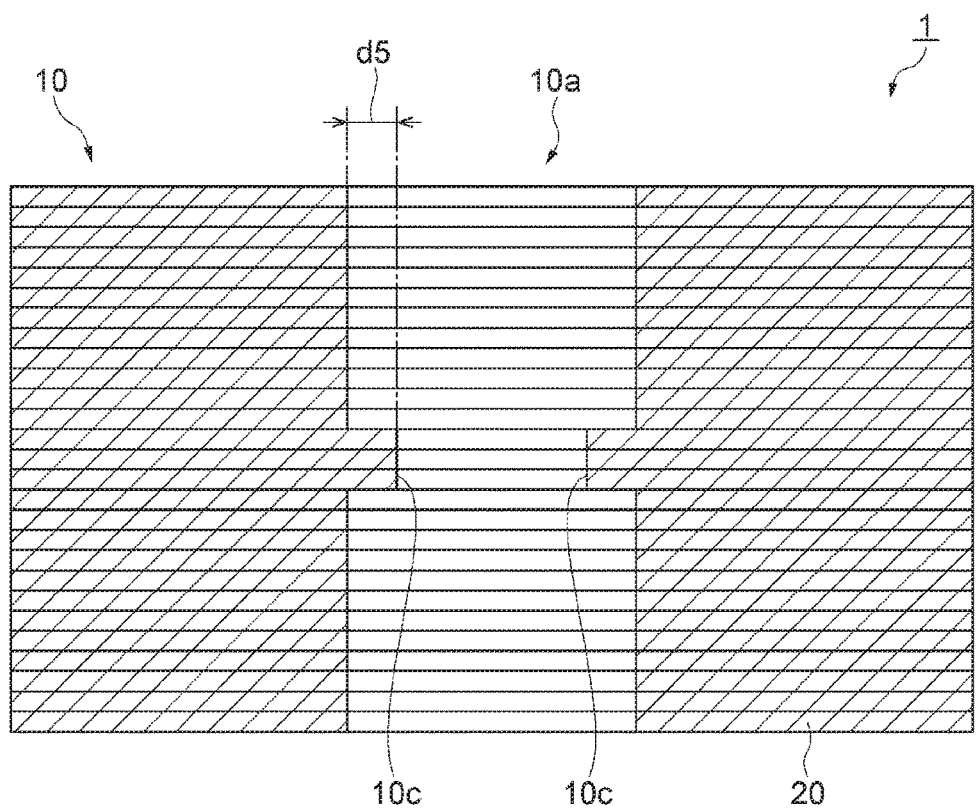
FIG. 9 is a perspective view showing another example of a laminated iron core.

As shown in FIG. 9, the deformed part 10c may be a projected part projected from an inner peripheral surface of the shaft hole 10a toward the radial inside (the side of the central axis Ax) like the projection 10d. In this case, the size of the deformed part 10c calculated by the controller 36 includes, for example, the height d1 of the deformed part 10c, the length d2 from the lower surface (inlet of the shaft hole 10a) of the laminated iron core 10 to the deformed part 10c in the lamination direction, the width d3 of the deformed part 10c, and a projection length d5 of the deformed part 10c.

Figure 10:
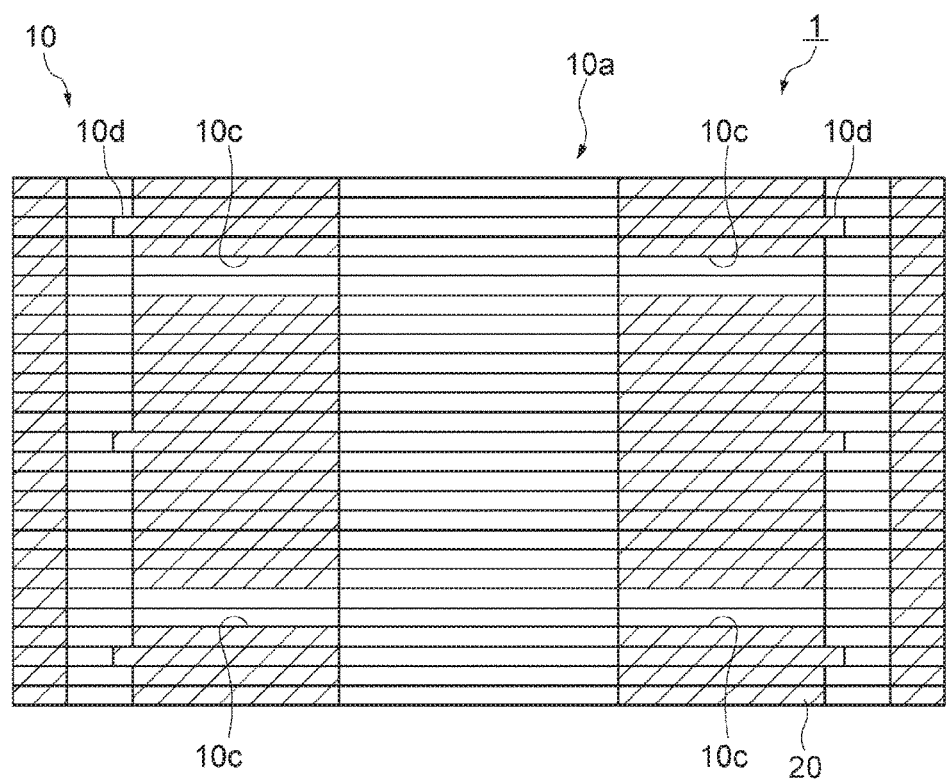
FIG. 10 is a perspective view showing a further example of a laminated iron core.
Figure 11:
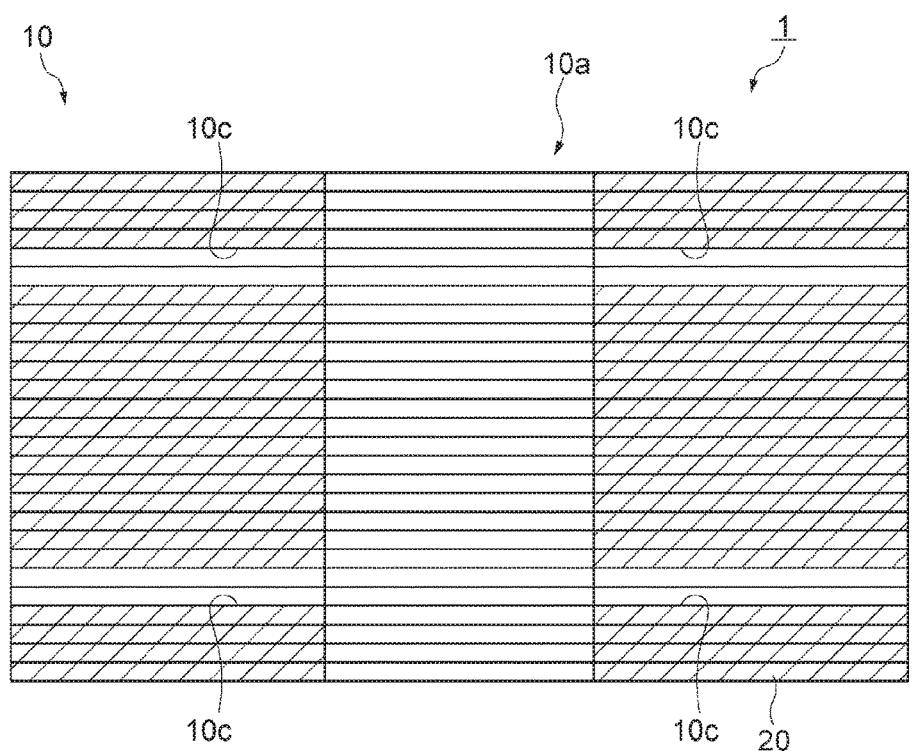
FIG. 11 is a perspective view showing a further example of a laminated iron core.

As shown in FIGS. 10 and 11, the deformed part 10c may be a branched hole radially continuing from the inner peripheral surface of the shaft hole 10a so as to be branched from the shaft hole 10a. In FIG. 10, the deformed part 10c joins the shaft hole 10a to the magnet-insert hole 10b. In FIG. 11, the deformed part 10c is pierced from the shaft hole 10a to an outer peripheral surface of the laminated iron core 10. The deformed part 10c may be a branched hole (not shown) continuing from an inside inner peripheral surface of the magnet-insert hole 10b in the radial direction (the side of the central axis Ax or the side of the outer peripheral surface of the laminated iron core 10) so as to be branched from the magnet-insert hole 10b.

A plurality of places of one deformed part 10c may be measured while gradually shifting measurement places by the non-contact sensor 38. In this case, even when the deformed part 10c has foreign substances such as burrs, the size of the deformed part 10c can be acquired with the foreign substances avoided by measuring the plurality of places of the deformed part 10c.

The deformed part 10c may be measured by the non-contact sensor 38 before the magnet-insert hole 10b of the laminated iron core 10 is provided with the permanent magnet 12 and the resin material 14 (that is, in a state of only the laminated iron core 10), or after the magnet-insert hole 10b of the laminated iron core 10 is provided with the permanent magnet 12 and the resin material 14 (that is, in a state of the completion of the rotor 1).

The hole such as the shaft hole 10a provided with the deformed part 10c or the magnet-insert hole 10b provided with the projection 10d has only to be opened in one of the upper and lower surfaces of the laminated iron core 10, and does not need to be a through hole. The non-contact sensor 38 may be provided over or under the hole at a side which is open in order to send or receive a detection signal from the non-contact sensor 38 through the hole.

The shape of the deformed part 10c is not particularly limited. That is, the sizes of the deformed parts 10c with various shapes can be acquired using at least the controller 36 and the non-contact sensor 38.

Also, the sizes of the deformed parts formed on the laminated iron cores constructing the stator as well as the rotor may be acquired using at least the controller 36 and the non-contact sensor 38.

Only for a purpose of reference, reference signs and numerals assigned to respective elements in this application are listed below.

1: ROTOR
10: LAMINATED IRON CORE
10a: SHAFT HOLE
10b: MAGNET-INSERT HOLE
10c: DEFORMED PART
10d: PROJECTION
20: BLANKED MEMBER (METAL PLATE)
30, 32: PINCHING PLATE
34: ACTUATOR
36: CONTROLLER (CALCULATOR)
38: NON-CONTACT SENSOR
10 Ax: CENTRAL AXIS
P: SURFACE PROFILE

What is claimed is:
1. A method for measuring a laminated iron core, comprising:
preparing a laminated iron core in which two or more kinds of metal plates with different shapes are laminated and a deformed part is formed inside a hole continuing in a lamination direction of the laminated iron core;

acquiring a surface profile data indicating a surface shape of the deformed part through an inlet of the hole by a non-contact sensor located in an outside of the hole; and calculating a size of the deformed part by a calculator based on the surface profile data.

2. The method according to claim 1, wherein the surface profile data indicating the surface shape of the deformed part is acquired by the non-contact sensor located in the outside of the hole through the inlet of the hole, with the laminated iron core pressurized in the lamination direction.

3. The method according to claim 1, wherein the non-contact sensor is a non-contact laser displacement meter, and the surface profile data indicating the surface shape of the deformed part is acquired by the non-contact laser displacement meter located in the outside of the hole, which applies laser light from the inlet of the hole to the deformed part and receives reflected light of the laser light.

4. The method according to claim 1, wherein the deformed part is a projected part projected from a peripheral surface of the hole in an intersection direction intersecting with the lamination direction.

5. The method according to claim 1, wherein the deformed part is a branched hole continuing from a peripheral surface of the hole in an intersection direction intersecting with the lamination direction so as to be branched from the hole.

6. The method according to claim 1, further comprising: moving or rotating one of the laminated iron core or the non-contact sensor with respect to the other of the laminated iron core and the non-contact sensor.

7. The method according to claim 1, wherein a length of the deformed part in the lamination direction is calculated by the calculator based on the surface profile data.

8. The method according to claim 1, wherein a length of the deformed part in a circumferential direction of the hole is calculated by the calculator based on the surface profile data.

9. The method according to claim 1, wherein a length from the inlet of the hole to the deformed part in the lamination direction is calculated by the calculator based on the surface profile data.

10. The method according to claim 1, wherein the deformed part is a projected part projected from a peripheral surface of the hole in an intersection direction intersecting with the lamination direction, and a projection length of the projected part is calculated by the calculator based on the surface profile data.

11. The method according to claim 2, wherein the non-contact sensor is a non-contact laser displacement meter, and the surface profile data indicating the surface shape of the deformed part is acquired by the non-contact laser displacement meter located in the outside of the hole, which applies laser light from the inlet of the hole to the deformed part and receives reflected light of the laser light.

12. The method according to claim 11, further comprising:
moving or rotating one of the laminated iron core or the non-contact sensor with respect to the other of the laminated iron core and the non-contact sensor.

13. The method according to claim 11, wherein a length from the inlet of the hole to the deformed part in the lamination direction is calculated by the calculator based on the surface profile data.

14. The method according to claim 2, further comprising:
moving or rotating one of the laminated iron core or the non-contact sensor with respect to the other of the laminated iron core and the non-contact sensor.

15. The method according to claim 14, wherein a length from the inlet of the hole to the deformed part in the lamination direction is calculated by the calculator based on the surface profile data.

16. The method according to claim 2, wherein a length from the inlet of the hole to the deformed part in the lamination direction is calculated by the calculator based on the surface profile data.

17. The method according to claim 3, further comprising:
moving or rotating one of the laminated iron core or the non-contact sensor with respect to the other of the laminated iron core and the non-contact sensor.

18. The method according to claim 17, wherein a length from the inlet of the hole to the deformed part in the lamination direction is calculated by the calculator based on the surface profile data.

19. The method according to claim 3, wherein a length from the inlet of the hole to the deformed part in the lamination direction is calculated by the calculator based on the surface profile data.

20. The method according to claim 6, wherein a length from the inlet of the hole to the deformed part in the lamination direction is calculated by the calculator based on the surface profile data.

* * * * *